United States Patent
Weber et al.

(10) Patent No.: US 9,227,041 B2
(45) Date of Patent: Jan. 5, 2016

(54) BALLOON CATHETERS WITH FIBERS FOR DELIVERY OF THERAPEUTIC AGENT AND METHODS OF MAKING THE SAME

(75) Inventors: Jan Weber, Maastricht (NL); John T. Clarke, Claregalway (IE); Aiden Flanagan, Kilcolgan (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 779 days.

(21) Appl. No.: 13/082,562

(22) Filed: Apr. 8, 2011

(65) Prior Publication Data

US 2011/0251590 A1    Oct. 13, 2011

Related U.S. Application Data

(60) Provisional application No. 61/322,451, filed on Apr. 9, 2010.

(51) Int. Cl.
*A61M 25/10* (2013.01)
*A61L 29/16* (2006.01)

(52) U.S. Cl.
CPC ............ *A61M 25/1002* (2013.01); *A61L 29/16* (2013.01); *A61L 2300/602* (2013.01); *A61L 2300/802* (2013.01); *A61L 2420/02* (2013.01); *A61M 2025/105* (2013.01); *A61M 2025/1031* (2013.01)

(58) Field of Classification Search
CPC . A61M 25/45; A61M 25/10; A61M 25/1002; A61M 2025/0056; A61M 2025/0057; A61M 2025/0058; A61M 2025/006; A61M 2025/1031; A61M 2025/105; A61M 25/0045; A61M 2300/802; A61M 2300/602; A61L 29/16; A61L 2420/02

USPC .............. 604/890.1, 508, 509, 96.01, 103.02, 604/103.06, 103.07, 103.08, 264, 265
See application file for complete search history.

(56) References Cited

U.S. PATENT DOCUMENTS

| | | | |
|---|---|---|---|
| 5,407,536 A | 4/1995 | Razac et al. | |
| 6,176,871 B1* | 1/2001 | Pathak et al. | ................. 623/1.21 |
| 7,459,192 B2 | 12/2008 | Parsonage et al. | |
| 2005/0037050 A1 | 2/2005 | Weber | |
| 2006/0079836 A1* | 4/2006 | Holman et al. | ............ 604/96.01 |
| 2007/0067882 A1 | 3/2007 | Atanasoska et al. | |
| 2007/0247033 A1* | 10/2007 | Eidenschink et al. | ........ 310/800 |
| 2008/0140002 A1* | 6/2008 | Ramzipoor et al. | ..... 604/103.02 |

(Continued)

OTHER PUBLICATIONS

C. Holtze et al., "Biocompatible Surfactants for Water-in-Fluorocarbon Emulsions," Lab Chip 8:1632-1639 (2008).

(Continued)

*Primary Examiner* — Andrew Gilbert
(74) *Attorney, Agent, or Firm* — Seager, Tufte & Wickhem, LLP

(57) ABSTRACT

A medical device comprises a catheter with an expandable member, fibers extending from the outer surface of the expandable member, and therapeutic agent coated on the fibers or carried in the spaces between the fibers. Upon expansion of the expandable member, the therapeutic agent is delivered from the medical device. A surfactant may be coated on the fibers. A method of manufacturing comprises coating the outer surface of an expandable member with a metallic layer, coating the metallic layer with at least one polymeric layer, forming a plurality of holes in at least one polymeric layer, forming fibers in the holes, and removing at least one polymeric layer.

12 Claims, 5 Drawing Sheets

(56) References Cited

U.S. PATENT DOCUMENTS

| | | | |
|---|---|---|---|
| 2008/0188825 A1* | 8/2008 | Atanasoska et al. | 604/509 |
| 2009/0030504 A1* | 1/2009 | Weber et al. | 623/1.42 |
| 2009/0069789 A1 | 3/2009 | Freyman et al. | |
| 2009/0143855 A1* | 6/2009 | Weber et al. | 623/1.42 |
| 2009/0318848 A1* | 12/2009 | Shippy, III et al. | 604/20 |
| 2010/0023047 A1* | 1/2010 | Simpson | 606/192 |
| 2010/0076377 A1* | 3/2010 | Ehrenreich et al. | 604/103.08 |
| 2010/0076401 A1* | 3/2010 | Von Oepen et al. | 604/509 |
| 2010/0081992 A1* | 4/2010 | Ehrenreich et al. | 604/103.02 |
| 2010/0185146 A1* | 7/2010 | Ramzipoor et al. | 604/103.02 |
| 2010/0318020 A1 | 12/2010 | Atanasoska et al. | |
| 2011/0137155 A1 | 6/2011 | Weber et al. | |
| 2011/0160659 A1* | 6/2011 | Clarke et al. | 604/103.02 |

OTHER PUBLICATIONS

M. Roussel et al., "Synthesis and Physico-Chemical Properties of Novel Biocompatible Alkyl D-Mannopyranosiduronate Surfactants Derived from Alginate," European J. of Organic Chemistry 14:3085-3094 (2005).

The Community Research and Development Information Service—CORDIS, National R&D Information Service (Spain), Novel lysine based-surfactants as analogues of partial glycerides and phospholipids, Abstract, Jun. 8, 2006, http://cordis.europa.eu/fetch?CALLER=MSS_ES_RESU_EN&ACTION=D&DOC=457&CAT=RESU&QUERY=0125cc469a6f:3495:3bd0ecc2&RDN=39627.

* cited by examiner

BALLOON CATHETERS WITH FIBERS FOR DELIVERY OF THERAPEUTIC AGENT AND METHODS OF MAKING THE SAME

CROSS REFERENCE TO RELATED APPLICATION

The present application claims priority to U.S. provisional application Ser. No. 61/322,451 filed Apr. 9, 2010, the disclosure of which is incorporated herein by reference in its entirety.

TECHNICAL FIELD

The present invention relates to medical devices, more particularly, to catheter devices.

BACKGROUND

Catheters are used in a wide variety of minimally-invasive or percutaneous medical procedures. For example, balloon catheters having drug coatings may be used to treat diseased target tissue, such as portions of blood vessels. Typically, for treatment of blood vessels, the balloon is inserted through a peripheral blood vessel and then guided via a catheter through the vascular system to the target intravascular site. However, as the balloon travels through the body, the flow of blood may wash away some of the drug coating, or the drug coating may otherwise become detached. This not only can result in an undesired loss of drug, but it can also result in drug being supplied to undesired parts of the body.

In certain drug delivery balloon catheters as have been proposed in the art, the surface of the balloon is coated with a coating containing the therapeutic agent to be delivered. When the balloon is expanded, the coating is pressed against the lumen wall, thereby delivering the drug. Such a system at times can be inefficient with respect to the delivery of the drug. Potential drawbacks that can be encountered with respect to drug delivery balloon catheters include not being able to deliver enough or the correct amount of the drug, not being able to deliver the drug quickly enough or in the desired time period, portions of the drug becoming dislodged during tracking of the catheter, and/or portions of the drug becoming dislodged during expansion of the balloon.

There is a continuing desire for improved catheter-based devices for drug delivery to a target site.

SUMMARY

In accordance with some embodiments of the disclosure, a medical device comprises a catheter with an expandable member mounted on the catheter, a plurality of fibers extending from the outer surface of the expandable member, the fibers having spaces between them, and a therapeutic agent coated on the fibers or carried in the spaces between the fibers. Upon expansion of the expandable member, the therapeutic agent is delivered from the medical device.

The medical device may further comprise a filler material carried in the spaces between the fibers. The medical device may further comprise a surfactant coated on the fibers. When the expandable member is expanded, the fibers may extend in a direction generally perpendicular to the longitudinal axis of the expandable member or in an angled direction with respect to the longitudinal axis of the expandable member.

In accordance with other embodiments of the disclosure, a method of manufacturing a medical device comprises manufacturing a catheter with a expandable member mounted on the catheter, attaching a plurality of fibers to the medical device, the fibers extending from the outer surface of the expandable member, the fibers having spaces between them, and applying a therapeutic agent to the medical device such that the therapeutic agent is coated on the fibers or carried in the spaces between the fibers.

In one embodiment of manufacturing the medical device, the step of attaching the fibers to the medical device may comprise the steps of coating the outer surface of the expandable member with a metallic layer, coating the metallic layer with at least one polymeric layer, forming a plurality of holes in at least one polymeric layer, forming fibers in the holes, and removing at least one polymeric layer.

In accordance with other embodiments of the disclosure, a method of delivering therapeutic agent to a target location within a body is provided, the method comprising: using a medical device comprising a catheter with a expandable member mounted on the catheter, a plurality of fibers extending from the outer surface of the expandable member, the fibers having spaces between them, and a therapeutic agent coated on the fibers or carried in the spaces between the fibers; tracking the expandable member to the target location within the body; and expanding the expandable member at the target location, thereby delivering the therapeutic agent from the medical device.

BRIEF DESCRIPTION OF THE DRAWINGS

FIG. 2a shows the balloon coated with a metallic layer. FIG. 2b shows a first polymeric layer coated on the metallic layer. FIG. 2c shows a second polymeric layer coated on the first polymeric layer. FIG. 2d shows holes formed in the two polymeric layers. FIG. 2e shows fibers formed in the holes. FIG. 2f shows the medical device after removal of the second polymeric layer.

DETAILED DESCRIPTION

Figure 1:
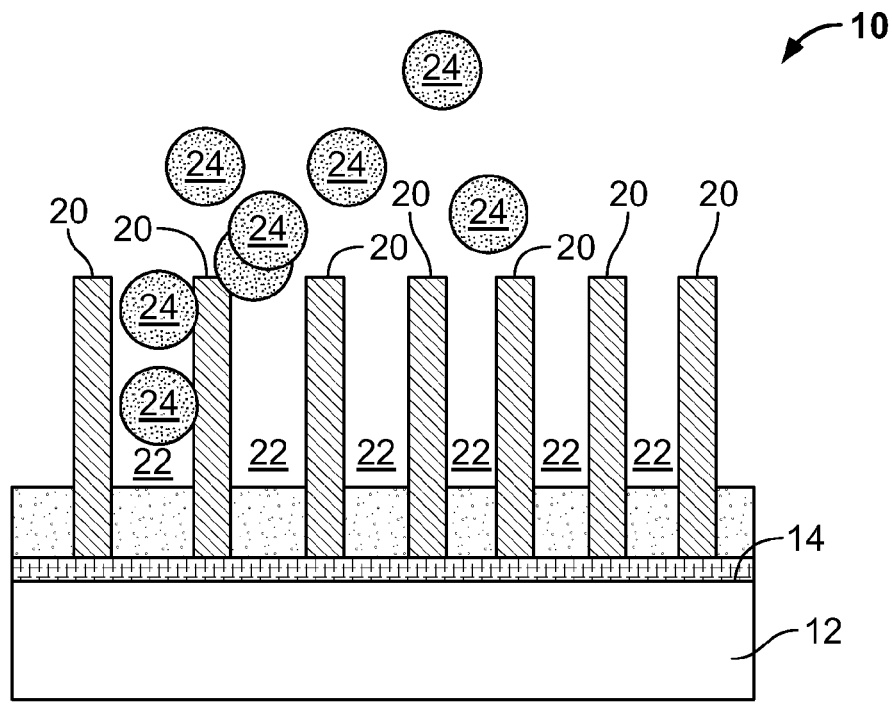
FIG. 1 shows a portion of an embodiment of a medical device with a plurality of fibers extending from the outer surface of a balloon.

FIG. 1 shows a portion of an embodiment of a medical device 10. The medical device 10 comprises an expandable member 12 with an outer surface 14. A plurality of fibers 20 extend from the outer surface 14 of expandable member 12. In the example of FIG. 1, the expandable member 12 is a balloon.

The balloon 12 may be mounted on the distal end of a catheter as is known in the art. Such catheter devices use an expandable balloon designed to be inserted in the body via a catheter and then expanded at a target site. Any of various mechanisms conventionally used for the delivery, actuation, or expansion (e.g., by inflation) of balloon catheter devices may be used. The balloon catheter may be designed similar to those that have been known in the art, including but not limited to angioplasty catheters, stent delivery catheters, inflation catheters, and/or perfusion catheters. The catheter devices of the present disclosure may be used in conjunction with other drug delivery devices, such as stents.

In the embodiment illustrated in FIG. 1, the plurality of fibers 20 that extend from the outer surface 14 of the balloon 12 have spaces 22 between them. As illustrated in FIG. 1, a therapeutic agent 24 is carried in the spaces 22 between the fibers 20. The fibers 20 can be relatively close together in order to carry and retain the desired amount of therapeutic agent 24 in the spaces 22 between the fibers 20. As described further herein, therapeutic agent 24 may additionally or alternatively be coated on the fibers 20.

A medical device as illustrated in FIG. 1 may be used as follows. A physician inserts the distal end of the catheter to which the balloon 12 is mounted into the patient by a manner known in the art. The physician then tracks the balloon 12 to the target location within the patient's body. Once at the target site, the physician then expands the balloon 12 at the target location, thereby delivering the therapeutic agent 24 from the medical device 10.

It will be appreciated that when the balloon 12 is being tracked to the target site, the balloon 12 is in an unexpanded condition of relatively small diameter. In this condition, the fibers 20 help maintain the therapeutic agent 24 in position and thereby help substantially prevent the therapeutic agent 24 from being washed off or otherwise becoming separated from the balloon 12 during delivery to the target site. Additionally, some or all of the fibers 20 may be protected underneath folds of the balloon 12 to further protect and help substantially prevent the therapeutic agent 24 from being washed off or otherwise becoming separated from the balloon 12 during delivery to the target site. In addition, a protective sheath, which may be removable or dissolvable, may also be placed over the balloon 12 and the fibers 20 to further protect and help substantially prevent the therapeutic agent 24 from being washed off or otherwise becoming separated from the balloon 12 during delivery to the target site.

When the catheter is at the target site, expansion of the balloon 12 can facilitate delivery of the therapeutic agent 24 from the medical device 10. The expansion, which in the case of a balloon may involve unfolding of the balloon, presses and/or brushes the fibers 20 against the target tissue, e.g., the vessel wall. This contact, or pressing and/or brushing, causes the therapeutic agent 24 to be transferred and thereby delivered from the medical device 10 to the target tissue. FIG. 1 shows some of the therapeutic agent 24 being delivered from the fiber brush.

Depending on the folding of the balloon 12 or other design features, the balloon 12 may undergo some rotation as it is being expanded. Such rotation also will cause a brushing of the fibers 20 against the target tissue. Again, such brushing can facilitate transfer of the therapeutic agent 24 from the medical device 10 to the target tissue.

A medical device with fibers for drug delivery as described herein can have one or more advantages over existing systems. In drug delivery from a balloon, one of the main objectives is achieving a good balance between the following parameters: having the balloon be able to carry a large drug load, the ability for a quick release of the drug when the balloon is expanded, protection of the drug particles from being washed off while being introduced in the body, and fine and uniform particles being released upon deployment. Certain currently proposed methods use a brittle matrix that just breaks upon deployment of the balloon. Such a system can have limitations in the amount of drug load it can carry, may require relatively prolonged expansion to achieve a desired amount of drug delivery, may result in particles of drug being washed off while being introduced in the body, and can deliver large and nonuniform pieces upon breaking of the coating.

A medical device with fibers for drug delivery as described herein can allow a large drug load to be taken on due to the ability of the fibers to hold the drug. In addition, the fibers can help protect the drug during transport and also can facilitate an even dispersion of the drug upon expansion. In instances wherein the fibers are brushed along the target surface, even dispersion of the drug is further facilitated.

FIGS. 2a-2f show steps in an embodiment of a method of manufacturing a medical device with a plurality of fibers extending from the outer surface of an expandable member such as a balloon. For certain embodiments of the medical device disclosed herein, it is desired to have fibers of a sufficient size to hold the drug particles that are intended to be carried. For example, it may be desired to disperse drug particles having a size of about 10 micrometers to about 20 micrometers. To do this, an example embodiment can have, for example, fibers on the same order of size or slightly bigger, for example about 10 micrometers or about 50 micrometers to about 150 micrometers in diameter or width.

By using a process as disclosed herein, fibers of a desired size can be attached to an expandable member wherein the fibers are well aligned, well connected, all of approximately the same length (if desired) and all pointing in the same direction (if desired). The result is a robust covering of fibers.

Figure 2A:
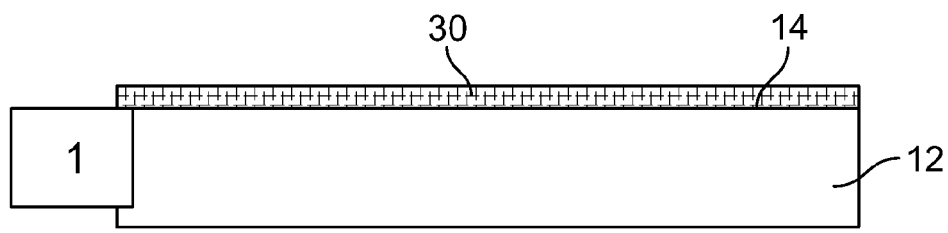
FIGS. 2a-2f show steps in an embodiment of a method of manufacturing a medical device with a plurality of fibers extending from the outer surface of a balloon.

FIG. 2a shows a first step in an example embodiment of a process for attaching fibers to an expandable member. In the first step in this embodiment, the outer surface 14 of a balloon 12 is coated with a metallic layer 30. This may be done by a sputtering process or other suitable process. In one example, the metallic layer 30 is gold, but other suitable materials may be used.

Figure 2B:
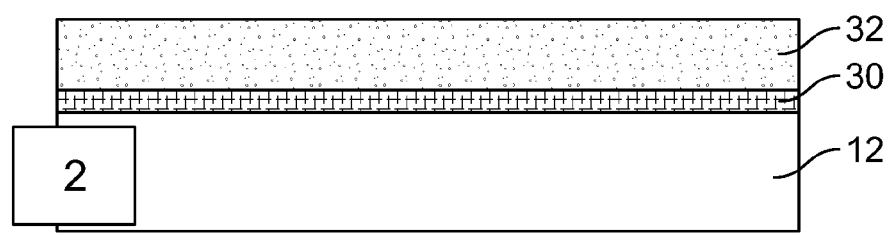
Figure 2C:
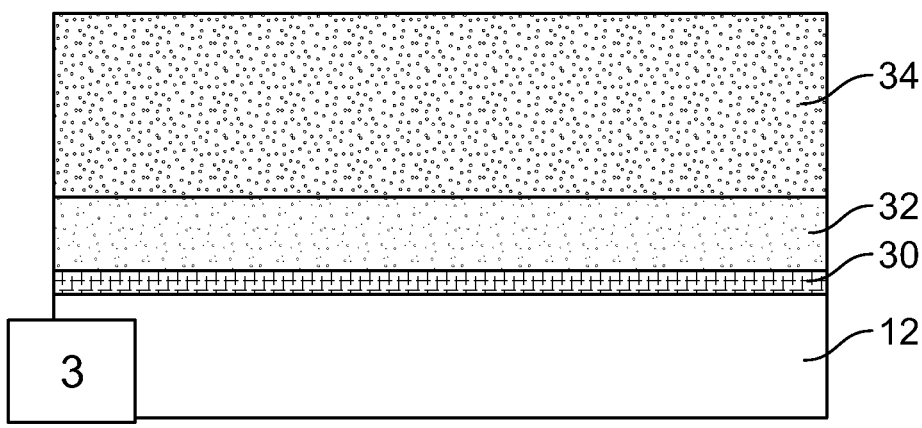

FIG. 2b shows a first polymeric layer 32 coated on the metallic layer 30. FIG. 2c shows a second polymeric layer 34 coated on the first polymeric layer 32. The first polymeric layer 32 may be, for example, a polypyrrole coating or a uniform closed polyurethane coating having a thickness on the order of about 10 micrometers. The second polymeric layer 34 may be, for example, a poly(ethylene-co-vinyl acetate) (PEVA) coating or a polyester coating on top of the first polymeric coating 32, having a thickness greater than the first polymeric coating 32. Other suitable materials and thicknesses may be used for the layers 32 and 34. The layers 32 and 34 may be formed by any suitable process, for example by electrochemical deposition or spray coating.

Figure 2D:
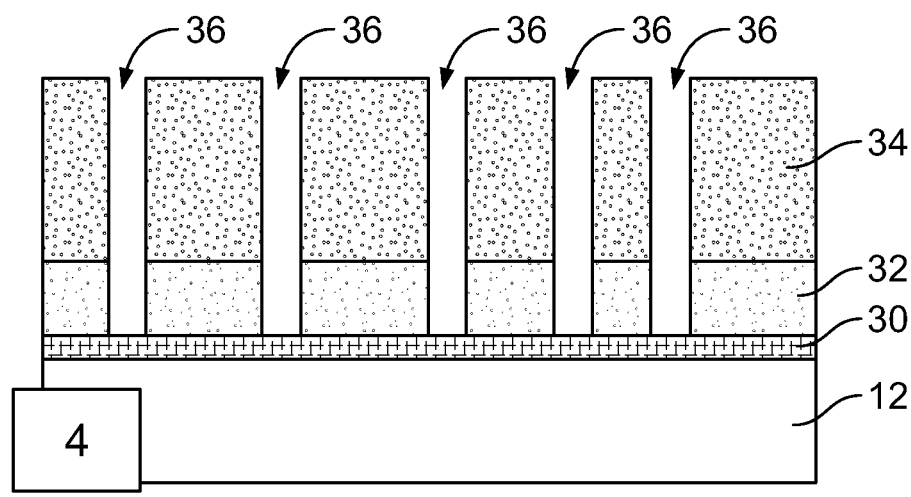

FIG. 2d shows a subsequent step in the process in which holes 36 are formed in the two polymeric layers 32 and 34. The holes 36 may be formed, for example, using an ablating process, such as laser ablating. By such laser ablation, one can drill micrometer-sized holes through the two polymer layers 32 and 34 to expose the metallic layer 36 underneath. The holes may be, for example, about 10 micrometers or about 50 micrometers to about 150 micrometers in diameter or width, or another suitable size. A process may be used to produce many holes 36 at the same time. For example, thousands of holes 36 may be made at the same time using a diffractive optical element. Other suitable processes for forming the holes 36 may be used.

Figure 2E:
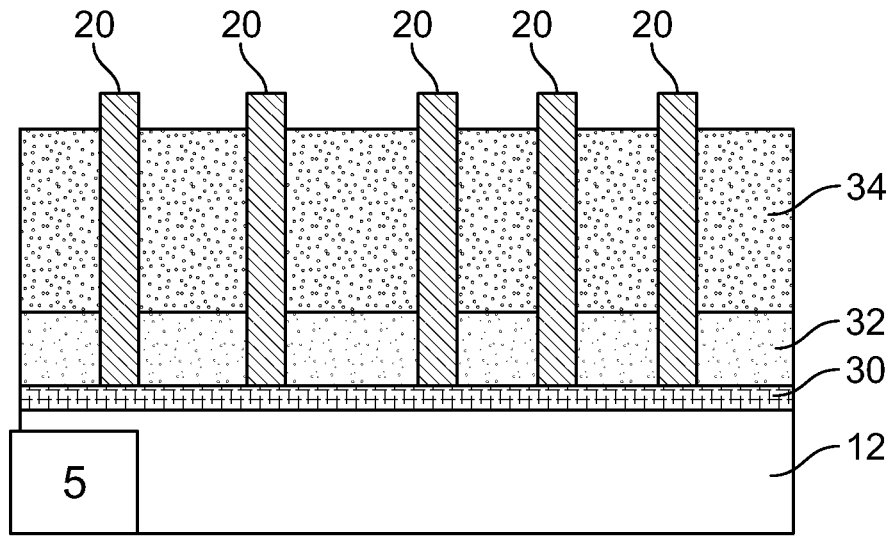

FIG. 2e shows fibers 20 formed in the holes 36. The fibers 20 may be formed of any suitable material, for example a polyester or polyamide material. The fibers 20 may be formed, for example, using an electro-polymerization process. Such a process may be used, if desired, to form the fibers 20 from an electroactive polymer such as a poylpyrrole. The width or diameter of the fibers 20 may be, for example, about 10 micrometers or about 50 micrometers to about 150 micrometers, or another suitable size.

Figure 2F:
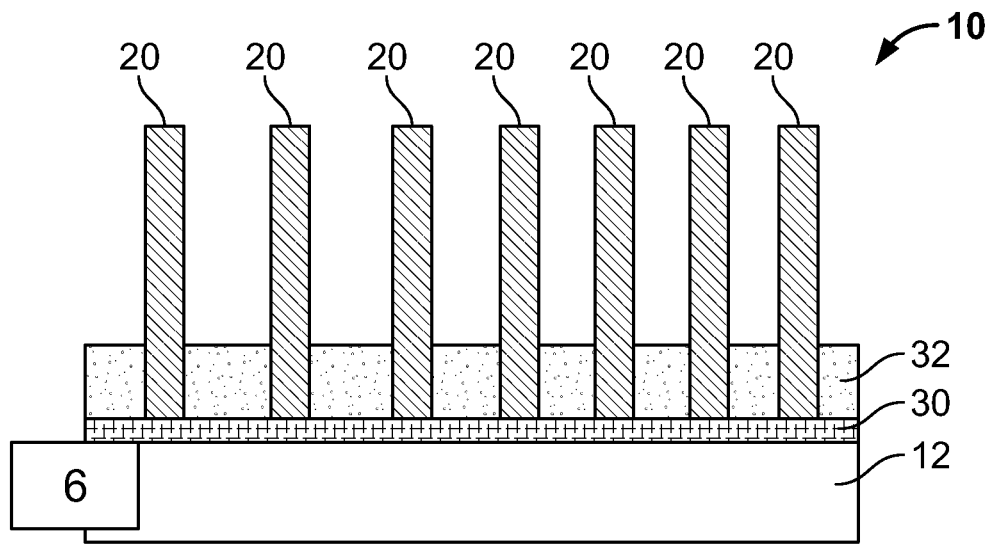

FIG. 2f shows the medical device 10 after removal of the second polymeric layer 34. The removal of this top coating exposes the upper part of the fibers 20, leaving the bottom part of the fibers 20 embedded within and supported by the first polymeric layer 32.

By using a process as disclosed herein, the size, orientation and spacing of the fibers can be controlled by controlling the size, orientation and spacing of the holes formed. Also, the strength of the connection between the fibers and the expandable member can be controlled by material and coating thickness selection.

Once the medical device is made with the fibers, the structure is loaded with drug or drug particles, of a type as described below or any other suitable type. In certain situations, the amount of drug to be carried by the medical device is substantially less than the fillable volume in the fiber brush. It may be desired, therefore, to mix the drug with a different filler substance, which can help fill the available volume, such that there is sufficient combined material to fill the entire brush. Many different substances may be used as a filler substance, e.g., dextran. The filler material may be carried in the spaces between the fibers or coated on the fibers.

Figure 3:
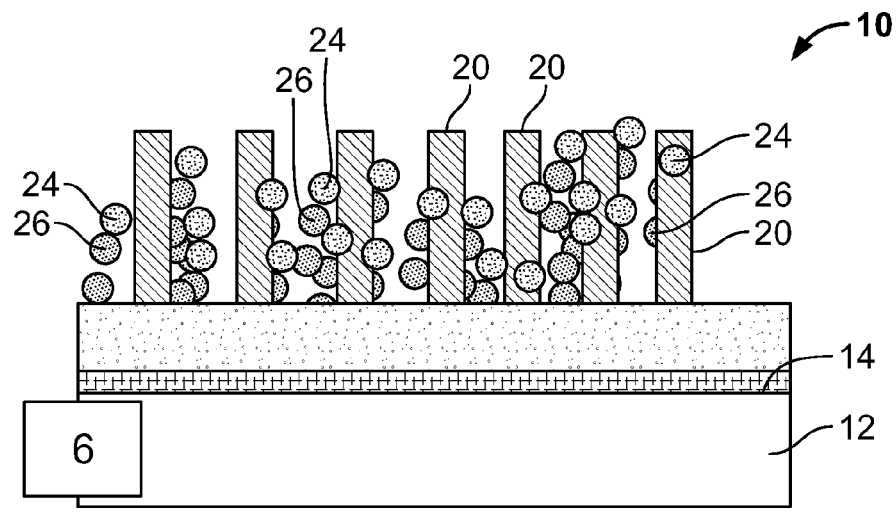
FIG. 3 shows the medical device of FIG. 2f after loading a therapeutic agent and an additional material.

Both the drug and the filler may be supplied and mixed in powder form. Then, the volume in the fiber brush can be filled by pushing the fiber brush on a surface having loose powder, filling up the entire brush, and then patting off the excess material. FIG. 3 shows the medical device 10 of FIG. 2f after loading a therapeutic agent 24 and an additional filler material 26.

Figure 4:
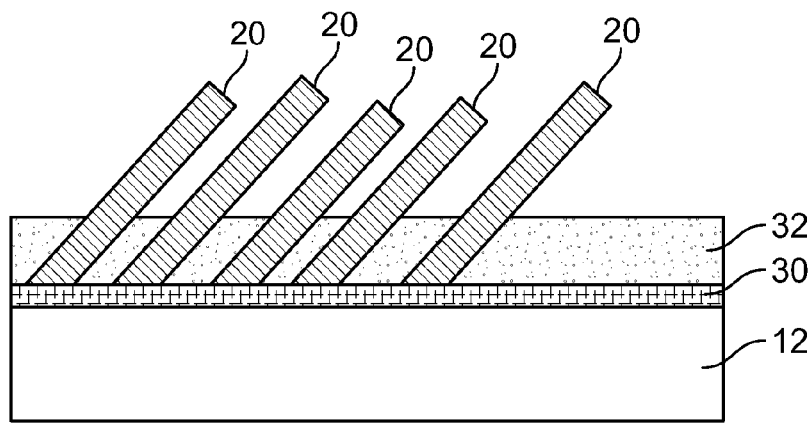
FIG. 4 shows an alternative embodiment in which the fibers extend in an angled direction with respect to the longitudinal axis of the balloon.

In the embodiment of FIG. 1, the fibers 20 extend in a direction generally perpendicular to the longitudinal axis of the balloon 12. FIG. 4 shows an alternative embodiment in which the fibers 20 extend in an angled direction with respect to the longitudinal axis of the balloon 12. The angle may be accomplished by simply creating the holes at the desired angle. In one example, the angle may be opposite the balloon folding direction such that the rotation and/or unfolding of the balloon will cause the fibers 20 to open up, thereby further exposing the therapeutic agent to facilitate drug delivery.

Figures 5A, 5B:
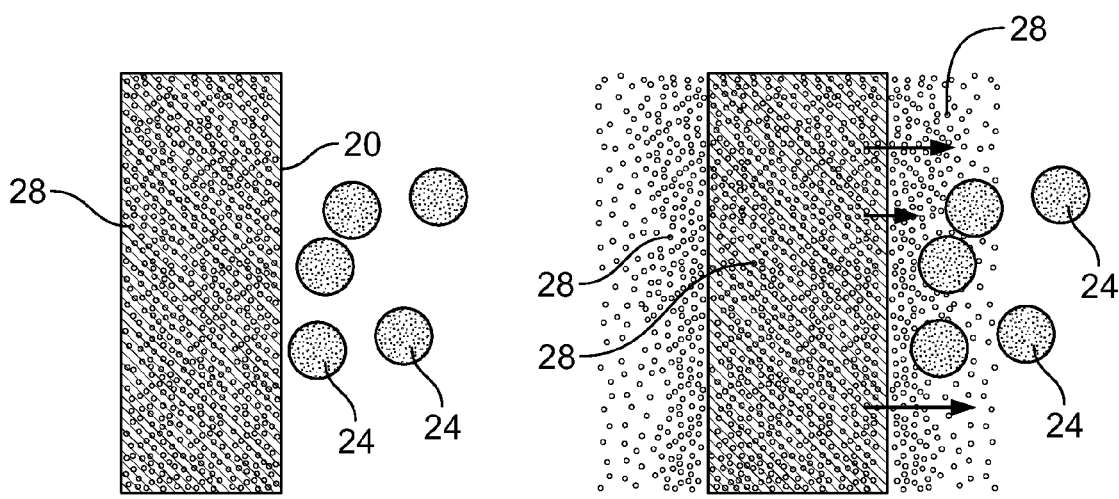
FIGS. 5a and 5b show therapeutic agent being delivered from an embodiment of a medical device with fibers comprising an electroactive polymer.

In some embodiments, the fibers 20 may be formed of an eleoctroactive polymer to facilitate drug delivery. Electroactive polymers are disclosed in U.S. Provisional Patent Application No. 61/074,456 (to which U.S. Patent Application Publication No. 2009/0318848 claims priority), U.S. Provisional Patent Application No. 61/185,745 (to which U.S. Patent Application Publication No. 2010/0318020 claims priority) and U.S. Provisional Patent Application No. 61/267,944 (to which U.S. patent application Ser. No. 12/962,962 claims priority), all of which are incorporated herein by reference. FIGS. 5a and 5b show therapeutic agent 24 being delivered from an embodiment of a medical device with fibers 20 comprising an electroactive polymer. Having the fibers 20 being from an electroactive polymer allows small molecules 28 to be driven directly from the fibers 20 in order to assist in dispersing the drug 24. As can be seen in FIG. 5a, the electroactive polymer fibers 20 have small molecules 28 embedded therein. These small molecules 28 may be, for example, detergent molecules that can be driven from the electroactive polymer upon activation.

When it is desired to deliver the drug 24, the electroactive polymer is activated. Activation may be accomplished by means known in the art, including those disclosed in U.S. Provisional Patent Application No. 61/074,456 (to which U.S. Patent Application Publication No. 2009/0318848 claims priority), U.S. Provisional Patent Application No. 61/185,745 (to which U.S. Patent Application Publication No. 2010/0318020 claims priority) and U.S. Provisional Patent Application No. 61/267,944 (to which U.S. patent application Ser. No. 12/962,962 claims priority), all of which are incorporated herein by reference. The activation of the electroactive polymer drives the small molecules 28 from the fibers, as shown in FIG. 5b. The small molecules help push the therapeutic agent 24 from the fibers 20 to deliver the therapeutic agent 24 to the target site.

Figure 6:
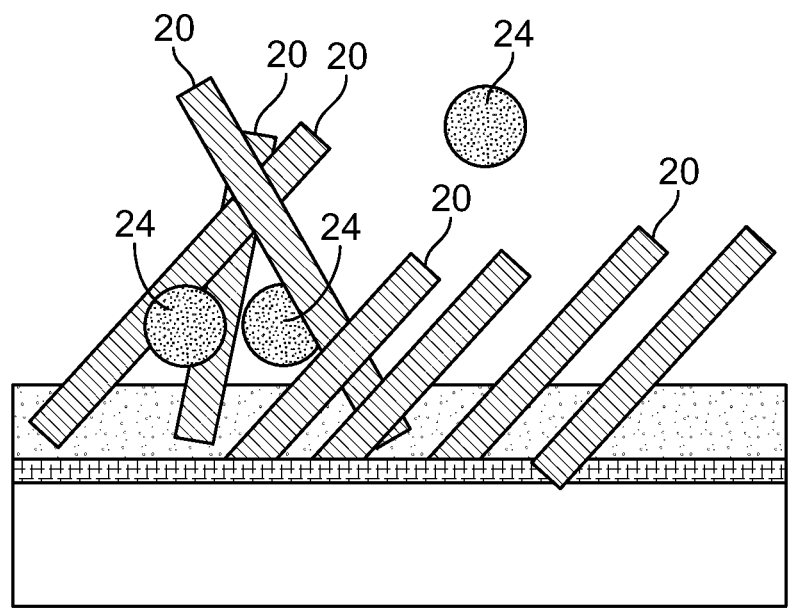
FIG. 6 shows an example in which the fibers are entangled.

In certain instances, it may be desired to coat the fibers 20 with a surfactant or other material that helps prevent entanglement of the fibers 20. FIG. 6 shows an example in which the fibers 20 are entangled. Tangled fibers 20 can prevent or slow down release of the drug particles 24 and/or can trap or sequester the drug particles 24 indefinitely in the fibers 20.

Figure 7:
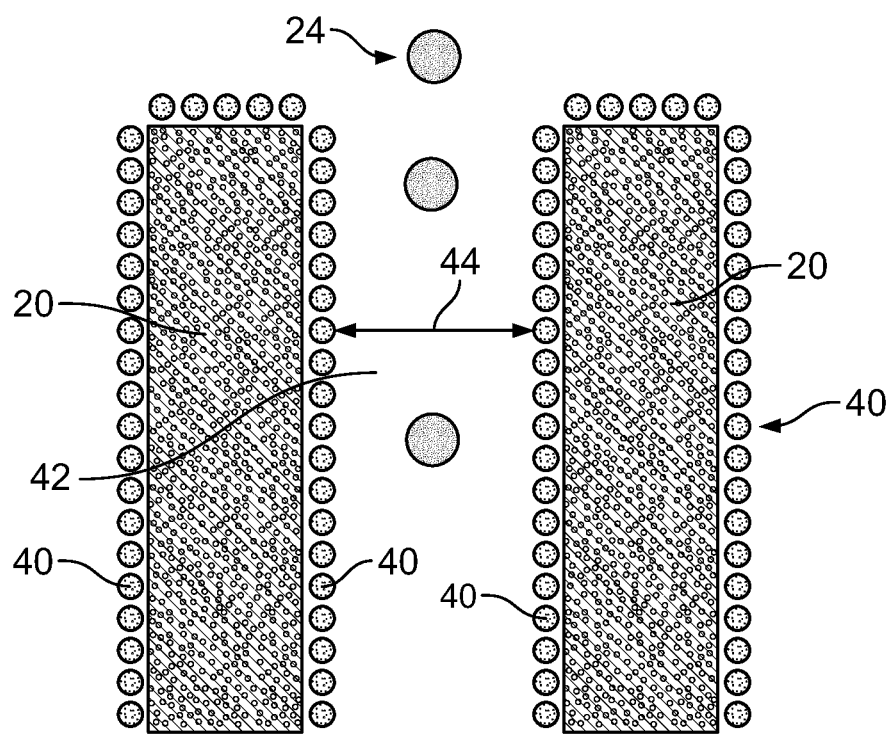
FIG. 7 shows fibers coated with a surfactant.

A way to keep the fibers 20 from getting tangled is to coat them with a material that helps prevent entanglement such as surfactant 40, as shown in FIG. 7. When fibers 20 coated with surfactant 40 are wetted by bodily fluids they will separate, because the surfactant 40 will reduce attractive forces between fibers 20. This will facilitate the release of drug 24 by keeping the fibers 20 apart and untangled. FIG. 7 shows the space 42 between adjacent fibers 20 being maintained at a desired spacing 44 to facilitate release of the drug particles 24. The surfactant 40 may be coated on the fibers 20 or carried in the spaces between the fibers 20.

The surfactant 40 may be selected based on the choice of fiber material. For example, polyester or polyamide fibers may be coated with silicone/divinylbenzene copolymer or PEG-based polymers. There are many surfactants available that may be used. Some examples are disclosed in C. Holtze et al., "Biocompatible Surfactants for Water-in-Fluorocarbon Emulsions," Lab Chip 8:1632-1639 (2008) and M. Roussel et al., "Synthesis and Physico-Chemical Properties of Novel Biocompatible Alkyl D-Mannopyranosiduronate Surfactants Derived from Alginate," European J. of Organic Chemistry 14:3085-3094 (2005).

The surfactant 40 may be applied in several ways. For example, the medical device with the fibers 20 may be dipped in a pre-mixed surfactant solution. Then the fibers 20 are allowed to dry, leaving a coating of surfactant 40 on the fibers 20. Thereafter, the fibers 20 may be loaded with the therapeutic agent 24, for example by dipping in drug solution, after which the device is again dried.

As an alternative method, the medical device with the fibers 20 may be dipped into solvent that will separate the fibers 20, using a hydrophobic or hydrophilic solvent as appropriate for the particular fiber material. Then the fibers 20 are allowed to dry. Thereafter, the fibers 20 may be loaded with the therapeutic agent 24, for example by dipping in a drug solution, after which the device is again dried.

As another alternative method, the medical device with the fibers 20 may be dipped into a solution comprising a solvent, a therapeutic agent 24 and a surfactant 40. Then the fibers 20 are allowed to dry.

Various combinations of methodologies can be used to coat fibers with surfactant and load them with drug.

The therapeutic agent used with embodiments of the disclosure may be any suitable pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds having a molecular weight of less than 100 kD. Exemplary cells include stem cells, progenitor cells, endothelial cells, adult cardiomyocytes, and smooth muscle cells. Further therapeutic agents that may be used with embodiments of the disclosure are disclosed in U.S. Provisional Patent Application No. 61/074,456 (to which U.S. Patent Application Publication No. 2009/0318848 claims priority), U.S. Provisional Patent Application No. 61/185,745 (to which U.S. Patent Application Publication No. 2010/0318020 claims priority) and U.S. Provisional Patent Application No. 61/267,944 (to which U.S. patent application Ser. No. 12/962,962 claims priority), all of which are incorporated herein by reference.

EXAMPLE 1

A coating layer of gold is applied to the outer surface of a catheter balloon by sputtering. A layer of polypyrrole is electrochemically applied to the gold layer by locating the balloon in a round beaker containing a 0.1 M pyrrole monomer aqueous solution having a circumferential silver (Ag) electrode spaced at equal distance from the balloon surface. Electropolymerization is then used to coat the balloon with a polypyrrole coating. The coated balloon is removed from the monomer solution and washed thoroughly with water. Then, a PEVA layer is spray-coated onto the polypyrrole layer using a toluene/PEVA solution. Using a laser and diffractors, holes are formed by laser ablation in the polymer coatings to create access to the gold. Then, another electropolymerization step is performed similar to the first, thereby forming polypyrrole fibers in the holes. The PEVA layer is removed with toluene, leaving poylpyrrole fibers supported by the polypyrrole layer.

EXAMPLE 2

A coating layer of gold is applied to the outer surface of a catheter balloon by sputtering. A layer of closed polyurethane is applied to the gold layer by spray coating to a thickness of 10 micrometers. A layer of polyester is coated on the polyurethane coating. Using a laser and diffractors, holes are formed by laser ablation in the polyester and polyurethane coatings. Using an electro-polymerization process, fibers are formed in the holes from a polyamide material. The polyester layer is removed, leaving fibers supported by the polyurethane.

The foregoing description and embodiments are not intended to be limiting. Each of the disclosed aspects and embodiments may be considered individually or in combination with other aspects, embodiments, and variations. Modifications of the disclosed embodiments incorporating the spirit and substance of the invention may occur to persons skilled in the art within the scope of the present invention.

We claim:

1. A medical device comprising:
   a catheter with an expandable balloon mounted on the catheter, the expandable balloon having an outer surface and being expandable from an unexpanded state to an expanded state;
   a plurality of fibers each having a proximal end and a distal end, the proximal ends affixed to the outer surface of the expandable balloon, each fiber of the plurality of fibers circumferentially and longitudinally spaced from any adjacent fiber to define a plurality of spaces extending radially away from the outer surface of the expandable balloon to the distal ends of the plurality of fibers when the expandable balloon is in the expanded state; and
   a therapeutic agent carried in the spaces between the plurality of fibers;
   wherein upon expansion of the expandable balloon the plurality of fibers are designed to be brushed against a target site to release the therapeutic agent from the spaces between the plurality of fibers and deliver the therapeutic agent from the medical device.

2. The medical device of claim 1, wherein the therapeutic agent is additionally coated on the plurality of fibers.

3. The medical device of claim 1, further comprising a surfactant.

4. The medical device of claim 3, wherein the surfactant is coated on the plurality of fibers.

5. The medical device of claim 1, wherein the expandable balloon comprises a longitudinal axis and when the expandable balloon is expanded the plurality of fibers extend in a direction generally perpendicular to the longitudinal axis of the expandable balloon.

6. The medical device of claim 1, wherein the plurality of fibers are polyester.

7. The medical device of claim 1, wherein the plurality of fibers are polyamide.

8. The medical device of claim 1, wherein the plurality of fibers are between about 10 micrometers and about 150 micrometers in width or diameter.

9. The medical device of claim 1, wherein the therapeutic agent is dispersed from the expandable balloon in particles having a size from about 10 micrometers to about 20 micrometers.

10. The medical device of claim 1, wherein the outer surface of the expandable balloon includes a metallic coating.

11. The medical device of claim 10, further comprising a polymeric layer disposed over the metallic coating, wherein the proximal ends of the plurality of fibers are embedded in the polymeric layer and contacting the metallic coating.

12. A method of delivering a therapeutic agent to a target location within a body, the method comprising:
   using a medical device comprising a catheter with an expandable balloon mounted on the catheter, the expandable balloon having an outer surface and being expandable from an unexpanded state to an expanded state, a plurality of fibers each having a proximal end and a distal end, the proximal ends affixed to the outer surface of the expandable balloon, each fiber of the plurality of fibers circumferentially and longitudinally spaced from any adjacent fiber to define a plurality of spaces extending radially away from the outer surface of the expandable balloon to the distal ends of the plurality of fibers when the expandable balloon is in the expanded state, and a therapeutic agent carried in the spaces between the plurality of fibers;
   tracking the expandable balloon to the target location within the body; and
   expanding the expandable balloon at the target location such that the plurality of fibers are brushed against the target location to release the therapeutic agent, thereby delivering the therapeutic agent from the medical device.

* * * * *